United States Patent [19]

Triebwasser

[11] 4,254,114
[45] Mar. 3, 1981

[54] CONTROL OF PYROPHOSPHATE MICROORGANISMS WITH ORGANOPHOSPHONATES

[75] Inventor: Keith C. Triebwasser, Cincinnati, Ohio

[73] Assignee: The Proctor & Gamble Company, Cincinnati, Ohio

[21] Appl. No.: 320

[22] Filed: Jan. 2, 1979

[51] Int. Cl.$^3$ .................... A01N 57/00; A61K 31/66
[52] U.S. Cl. .................................................... 424/204
[58] Field of Search ........................................ 424/204

[56] References Cited

U.S. PATENT DOCUMENTS

| | | | |
|---|---|---|---|
| 3,159,537 | 12/1964 | Takesue et al. | 167/55 |
| 3,671,644 | 6/1972 | Irani et al. | 424/346 |
| 3,683,080 | 8/1972 | Francis | 424/204 |
| 3,826,640 | 7/1974 | Theissen | 71/86 |
| 3,874,869 | 4/1975 | Koppensteiner et al. | 71/67 |
| 3,911,120 | 10/1975 | Mod et al. | 424/211 |
| 3,917,476 | 11/1975 | Kerst et al. | 71/67 |
| 3,965,265 | 6/1976 | Koppensteiner et al. | 424/204 |
| 4,067,971 | 1/1978 | Francis et al. | 424/204 |
| 4,083,972 | 4/1978 | Francis | 424/204 |
| 4,113,861 | 9/1978 | Fleisch et al. | 424/204 |
| 4,113,862 | 9/1978 | Fleisch et al. | 424/204 |
| 4,125,608 | 11/1978 | Blum et al. | 424/180 |

FOREIGN PATENT DOCUMENTS 777718  6/1957  United Kingdom .................... 424/204

OTHER PUBLICATIONS

Kato et al., C.A. vol. 81 (1974) 73,452f.
Takahashi et al., C.A. vol. 82 150,525g.
Derwent Pub. 83730v/48 11/6/74.
Indian Journal of Applied Chemistry 34(6) 249-252 (1971 Shuhla et al.
Gerstein et al., Antimicrobial Agents & Chemotherapy 7(3):255-258 (1975).
Translation of German Appl. 1,045,373 4/26/57.
Shopsis et al., J. Biol. Chem. 249(8): 2473-2477 (1974).
Kaye, *Nephron* 10(2-3): 188-194 (1973).
Britz et al., S. Afr. J. Dairy Technol. 8(2): 79-83 (1976).
Reeves et al., J. Biol. Chem. 249, 7737-7741 (1974).
Engel, Chem Review, 77: 349-367 (1977).
Wood, Federation Proceedings 36:2197-2205 (1977).
Milner et al., J. Biol. Chem. 253(3) 878-883 (1978).
Biochim. Biophys. Acta 220: 346-349 (1970).
Reeves, J. Biol. Chem. 243(11): 3202-3204 (1968).
Reeves et al., Biochem & Biophys. Res. Comm. 66(4) 1389-1395 (1975).
O'Brien et al., J. Biol. Chem. 250(22) 8690-8695 (1975).
Macy et al., J. Bacteriol. 134(1) 84-91 (1978).

*Primary Examiner*—Allen J. Robinson
*Attorney, Agent, or Firm*—Donald E. Hasse; Michael J. Roth; Richard C. Witte

[57] ABSTRACT

A method of selectively controlling pyrophosphate-utilizing microorganisms comprises contacting said microorganisms with an organism controlling amount of certain organophosphonate compounds. Accordingly, a method of treating amoebiasis in a human or lower animal comprises administering to a human or lower animal in need of such treatment a safe and effective amount of such organophosphonate compound. Similarly, a method of selectively controlling *Propionibacteria* species in the manufacture of cheese comprises incorporating an organism controlling amount of an organophosphonate compound in the raw materials for said cheese.

2 Claims, No Drawings

CONTROL OF PYROPHOSPHATE MICROORGANISMS WITH ORGANOPHOSPHONATES

TECHNICAL FIELD

Organophosphonate compounds are used to control certain amoeba and other microorganisms which metabolize pyrophosphate.

Amoebiasis is an infection produced by *Entamoeba histolytica*. It is an asymptomatic carrier state in most individuals, but diseases ranging from chronic, mild diarrhea to fulminant dysentery are frequently produced. Among extraintestinal complications, the most common is hepatic abscess, which may rupture into the peritoneum, pleura, lung, or pericardium.

Amoebiasis is a disease of world-wide occurrence, and can no longer be considered a tropical disease. In some temperate regions where sanitary conditions are poor, the incidence may be almost as high as in tropical countries. The disease is widespread in the United States, and surveys have shown an incidence of 20% or more in inhabitants of institutions and in some rural areas. In areas where standards of hygiene are higher the incidence is much less, but nonetheless quite significant. The disease occurs in infants and children as well as in adults.

*E. histolytica* is an organism characterized by its use of inorganic pyrophosphate as an energy source in its metabolism in place of adenosine triphosphate (ATP). Other important microorganisms which show this characteristic include *Propionibacterium shermanii* which is involved in the fermentation of Swiss cheese; certain species of *Acetobacter*, involved in the conversion of fruit juices to vinegar; and the photosynthetic bacterium *Rhodospirillum rubrum*.

The present invention provides a means for controlling the pyrophosphate-using microorganisms such as *E. histolytica* in a selective manner, and without interrupting the metabolism of non-pyrophosphate utilizing organisms. While not intending to be limited by theory, it is hypothesized that the pyrophosphate-using microorganisms "mistake" the P-C-P bond of the geminal organophosphonates for the P-O-P bond of pyrophosphate, and imbibe the organophosphonate (which cannot be used as an energy source), whereupon metabolism ceases.

BACKGROUND ART

Wood, H. G., *Federation Proceedings* 36:2197–2205 (1977) reviews the metabolism of several pyrophosphate-utilizing organisms.

*Chemical Review* 77:349–367 (1977) discusses possible uses of phosphonates as analogs of natural phosphates.

*J. Biol. Chem.* 249:7737–7741 (1974) discusses the pyrophosphate dependent phosphofructokinase of *Entamoeba histolytica*.

T. J. Britz, et al., *S. Afr. J. Dairy Technol.*, 8(2):79–83 (1976) describes detection of propionibacteria as the causative organisms of defects in Gouda cheese.

A series of U.S. patents to M. D. Francis describes the use of phosphonates to treat various diseases involving bone mineral. See, for example, U.S. Pat. No. 3,683,080.

The biological activity of phosphonate compounds in areas other than those involving bone mineral is also known. The following references are illustrative of some of the types of biological responses described in the literature for phosphonate compounds.

Canadian Pat. No. 753,207 (Monsanto) discloses polyphosphonates, including EHDP, as a potentiator for phenolic and quat bactericides used in sanitizing, antiseptic and cosmetic compositions. U.S. Pat. No. 3,671,644 appears to be the counterpart of Canadian Pat. No. 753,207.

German 1,045,373 (Hoechst; 1957) discloses diphosphonic acids and their use in cosmetic products, as stabilizers for antibiotics such as penicillin, and for the prevention of blood coagulation.

U.S. Pat. No. 3,874,869 (Henkel; 1973) discloses the use of EHDP in combination with diamino antimicrobials to provide synergistic microbiocidal results.

Kaye, M., *Nephron* (1973), 10(2–3), 188–94 discloses tests of EHDP (ineffectual) in the treatment of hyperparathyroidism.

U.S. Pat. No. 3,159,537 (American Cyanamid; 1960) discloses various phosphonic acid derivatives as potentiators for tetracycline antibiotics.

3,4-dihydroxybutyl-1-phosphonate is disclosed as an inhibitor of phosphatidyl glycerol synthesis in *E. coli*. Shopsis, et al., *J. Biol. Chem.* (1974), 249(8), 2473–7.

The use of phosphonoacetic acid in the treatment of herpes simplex is disclosed in "Antimicrobial Agents in Chemotherapy" (1975), 7(3), 285–8, by Gerstein, et al.

The use of phosphonic acids (generally monophosphonates) as herbicides, plant growth regulators, and the like, is disclosed in a variety of publications, including U.S. Pat. No. 3,826,640, *Indian Journal of Applied Chemistry* (1971), 34(6), 249–52; Japanese Patent 74/40936 (CA 82 150525 g) and CA 81 73452f.

The use of phosphonates as algicides is disclosed in U.S. Pat. No. 3,917,476 (1975) and the use of phosphonates to inhibit fungi and bacteria is disclosed in U.S. Pat. No. 3,911,120 (1975).

DISCLOSURE OF THE INVENTION

The present invention provides a method for selectively controlling pyrophosphate-utilizing microorganisms comprising contacting such microorganisms with an organism-controlling amount of a geminal organophosphonate compound of the type disclosed more fully hereinafter.

Because *E. histolytica*, the causative agent of amoebic dysentery, is a pyrophosphate utilizing organism, the present invention also provides a method for treating amoebic dysentery in a human or lower animal comprising administering to the human or lower animal in need of such treatment a safe and effective amount of an organophosphonate compound.

By "pyrophosphate utilizing microorganism" is meant those organisms which utilize inorganic pyrophosphate to replace the functions of adenosine triphosphate as a source of energy in metabolism.

By "controlling" is meant inhibiting or killing the microorganism. Since the organophosphonates appear to act by serving as inert substrates for certain metabolic enzymes, thus disrupting the metabolic processes of the microorganism, the difference is not medically or industrially significant since in either event the microorganisms are rendered inactive, and incapable of exerting their usual deleterious effects.

By an "effective amount" of organophosphonate compound is meant an amount of the compound sufficient to achieve the desired benefit, e.g., control of amoebic dysentery in a patient in need of such treatment. It will be appreciated that the amount of the organophosphonate compound and the treatment regimen will vary, depending upon the patient, the severity of the disease state, and like factors which must be considered by the attending physician.

By a "safe" amount of the organophosphonate compound is meant that the benefit:risk ratio attendant with the administration of the organophosphonate compound is judged to be acceptable, according to the precepts of sound medical practice. Typical examples of such levels to be used in the present process are disclosed in more detail hereinafter, but it is to be understood that these can be modified by the attending physician according to the needs of individual patients.

By "administration" of the organophosphonate compounds is meant systemic use, as by injection, intravenous infusion, and, preferably, oral administration thereof, as well as by directly contacting the target microorganisms with the compounds, as by lavage or enema.

The organophosphonate compounds (or, more succinctly, "phosphonates" or "diphosphonates") employed in the manner of this invention are, chemically, of the geminal diphosphonate type.

The geminal phosphonate compounds which are employed in the present invention are characterized by the phosphonate moiety $-PO_3M_2$, wherein M represents H or a pharmaceutically-acceptable cation or ester group. The phosphonates herein are organophosphonates, i.e., the phosphonate moiety is attached to a carbon atom by a carbon-phosphorus bond (C-P bond). The carbon atom, in turn, is bonded to other hydrocarbyl groups, e.g., alkyl phosphonates, or to hydrogen atoms, e.g., methane phosphonates, or to mixed hydrocarbyl groups, hydrogen atoms or other substituents, e.g., haloalkyl phosphonates. The hydrocarbyl groups can be substituted or non-substituted alkyl (including cycloalkyl), aryl (including heteroaryl) and the like. Substituent groups on the alkyl or aryl hydrocarbyl moiety can be, for example, additional phosphonate moieties: halogens, especially chlorine; carboxyl; esterified carboxyl; hydroxyl; amino; amido; and the like. Used herein are those organophosphonates having more than one $C-PO_3M_2$ group, i.e., diphosphonates, more specifically geminal diphosphonates, and are characterized by having in their structures at least one geminal diphosphonate grouping of the type

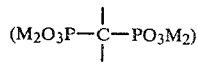

Typical compounds useful herein are of the general formula

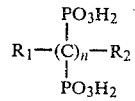

wherein n is an integer from 1 to about 10 and the substituent groups $R_1$ and $R_2$ are H, alkyl, aryl, alkenyl, and the like. Examples of such phosphonates are those wherein $R_1$ is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., chlorine, bromine and fluorine), amino, substituted amino (e.g., dimethylamino, diethylamino, N-hydroxy-N-ethylamino, acetylamino), $-CH_2COOH$, $-CH_2PO_3H_2$, $-CH(PO_3H_2)(OH)$ or $-CH_2CH(PO_3H_2)_2$; $R_2$ is hydrogen, lower alkyl (e.g., methyl, ethyl, propyl and butyl), amino, benzyl, halogen (e.g., chlorine, bromine and fluorine), hydroxyl, $-CH_2COOH$, $-CH_2PO_3H_2$, or $-CH_2CH_2PO_3H_2$, or a pharmaceutically-acceptable salt thereof such as alkali metal (e.g., sodium and potassium), alkaline earth metal (e.g., calcium and magnesium), non-toxic heavy metal (e.g., stannous and indium), and ammonium or low molecular weight substituted ammonium (e.g., mono-, di-, and triethanolammonium) salts. It will be appreciated that groups $R_1$ and $R_2$ can be cycloalkyl, heterocyclic or can be joined in ring structures, said rings being carbocyclic or heterocyclic.

Among the operable phosphonates encompassed by the above formula are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid (dichloromethylene diphosphonic acid); nonane-5,5-diphosphonic acid; n-pentane-1,1-diphosphonic acid; methanedifluorodiphosphonic acid, methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphonoprop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-hydroxyethyl)-aminomethanediphosphonic acid; N-acetylaminomethanediphosphonic acid; aminomethanediphosphonic acid; and the pharmaceutically-acceptable salts of these acids, e.g., sodium, potassium, calcium, magnesium, stannous, indium, ammonium, triethanolammonium, diethanolammonium and monoethanolammonium salts.

Mixtures of any of the foregoing phosphonic acids and/or salts can be used in the practice of this invention.

Ethane-1-hydroxy-1,1-diphosphonic acid, an especially preferred geminal phosphonate, has the molecular formula $CH_3C(OH)(PO_3H_2)_2$ (according to nomenclature by radicals, the acid might also be named 1-hydroxyethylidene diphosphonic acid). The most readily crystallizable salt of this acid is obtained when two or three of the acid hydrogens are replaced by sodium. Preferred salts for the purpose of this invention are the trisodium hydrogen salt which has the structure:

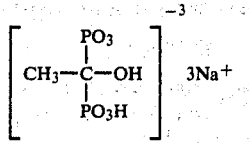

and the disodium dihydrogen salt.

The trisodium hydrogen salt normally crystallizes as the hexahydrate which loses some water during air-drying to yield a mixture of the hexa- and monohydrate averaging 3 to 4 molecules of water of hydration.

While any pharmaceutically-acceptable salt of ethane-1-hydroxy-1,1-diphosphonic acid can be used in the practice of this invention, the tetrasodium salt, the trisodium hydrogen salt, the disodium dihydrogen salt, the monosodium trihydrogen salt, and the mixtures thereof are preferred. The other sodium, potassium, ammonium, and mono-, di-, and triethanolammonium salts and mixtures thereof are also suitable, provided caution is observed in regulating the total intake of cation species in the salt composition. These compounds can be prepared by any suitable method; however, an especially preferred method is disclosed in U.S. Pat. No. 3,400,149, Quimby and Prentice, Sept. 3, 1968, incorporated herein by reference.

Methanehydroxydiphosphonic acid and related compounds operable herein can be prepared, for example, by the reaction of phosgene with an alkali metal dialkyl-phosphite. A complete description of these compounds and the method for preparing same is found in U.S. Pat. No. 3,422,137, Quimby, Jan. 14, 1969, incorporated herein by reference.

Methanediphosphonic acid and related compounds useful herein are described in detail in U.S. Pat. No. 3,213,030, Diehl, Oct. 19, 1965; a preferred method of preparing such compounds is disclosed in U.S. Pat. No. 3,251,907, Roy, May 17, 1966, incorporated herein by reference.

Ethane-1,1,2-triphosphonic acid and related compounds which can be used in this invention, as well as a method for their preparation, are fully described in U.S. Pat. No. 3,551,339, Quimby, Dec. 29, 1970, incorporated herein by reference.

Propane-1,1,3,3-tetraphosphonic acid and related compounds useful herein, and a method for preparing same are fully disclosed in U.S. Pat. No. 3,400,176, Quimby, Sept. 2, 1968, incorporated herein by reference.

Pentane-2,2-diphosphonic acid and related compounds can be prepared in accordance with the method described by G. M. Kosolopoff in *J. Amer. Chem. Soc.* 75, 1500 (1953), incorporated herein by reference.

Substituted ethane diphosphonic acids and salts and esters thereof are disclosed in U.S. Pat. No. 3,940,436, Kerst, Feb. 24, 1976, the disclosures of which are incorporated herein by reference. U.S. Pat. No. 3,944,599, Mar. 16, 1976, to the same inventor, discloses geminal diphosphonate compounds having halogen and hydroxyl substituent groups, and the means for preparing same. The disclosures of this patent are also incorporated herein by reference.

Phosphonobutane tri- and tetra-carboxylic acid compounds and their preparation are disclosed in U.S. Pat. Nos. 3,886,204 and 3,886,205, Geffers, et al., both issued May 27, 1975, the disclosures of which are incorporated herein by reference.

German 2360-798 to Henkel & Cie GmbH, June 26, 1975, discloses pharmaceutical and cosmetic preparations for influencing the deposition of poorly soluble calcium salts, said preparations comprising polymethylene phosphonic acid compounds. This publication, the disclosures of which are incorporated herein by reference, describes the preparation of the phosphonate materials in detail.

The preparation and pharmacological properties of various amino phosphonate compounds are described in German 2343-146 (Mar. 6, 1975); Belgian 822-930 (June 4, 1975); Belgian 822-929 (June 4, 1975); German 2360-711 (June 12, 1975); German 2360-719 (June 12, 1975); Belgian 819-187 (Feb. 26, 1975); Belgian 819-188 (Feb. 26, 1975); and Belgian 819-189 (Feb. 26, 1975), the disclosures of said publications being incorporated herein by reference.

Other geminal diphosphonates useful herein include the carbonyl diphosphonates (fully disclosed in U.S. Pat. No. 3,497,313, incorporated herein by reference) and 3-aminopropane-1,1-diphosphonates.

As can be seen from the foregoing, the preparation of the phosphonates used in the practice of this invention can be accomplished using well-known methods, or by simple modifications of various art-disclosed procedures. Only those organophosphonates which are pharmaceutically-acceptable (i.e., provide a satisfactory benefit:risk ratio) are contemplated for use herein.

BEST MODE OF PRACTICING THE INVENTION

As discussed above, when the organophosphonate compounds are used to treat amebiasis, the dosage and administration schedules should be determined by a physician thoroughly familiar with the acute and chronic management of amoebic disease, and a number of factors will enter into the selection of an optimal therapeutic regimen. However, in therapy with a commercially available, pharmaceutical grade organophosphonate compound such as ethane-1-hydroxy-1,1-diphosphonate disodium (NaEHDP), the following general guidelines should be followed. The recommended initial dose of NaEHDP for most patients is 0.1–5 milligrams/kilogram body weight/day, although higher dosages may be used. Dosages of NaEHDP above 10 milligrams/kilogram should be reserved for use when urgent control of amoebic dysentery is necessary. Treatment with NaEHDP at doses above 10 milligrams/kilogram/day should not exceed three months duration. Dosages of NaEHDP in excess of 20 milligrams/kilogram/day are not recommended, although in certain intractable cases, higher dosages may prove necessary, for brief periods.

The organophosphonate compound employed in the practice of this invention is preferably administered as a single, oral dose, two hours before meals if significant systemic absorption is desired. It may be given with fruit juice or water. Food, particularly materials high in calcium content such as milk, in the stomach or upper portions of the small intestine may reduce systemic absorption. Therefore, if systemic absorption of the organophosphonate compound is indicated in the particular amoebic state being treated, eating should be avoided for two hours before and after drug administration.

In the treatment of amoebic dysentery caused by *E. histolytica* an advantage of the organophosphonate compounds employed in the present invention is that they are sparingly absorbed from the gastrointestinal tract. Thus, they naturally remain at the anatomic situs where their pharmacologic effects are most needed for the treatment of amoebic dysentery. In addition, this biochemical feature makes the organophosphonate compounds especially useful in combination therapy with other amoebicides which are more effective systemically than intraluminally.

Other compounds are well known for the chemotherapy of amoebiasis. The chemical structures, pharmacological effects, therapeutic uses and other characteristics of such drugs are fully discussed in the *Pharmacological Basis of Therapeutics*, 5th ed. (1975) Lewis S. Goodman and Alfred Gilman, Ed., in chapters 53 and 54, by Ian M. Rollo. Of the compounds now used to treat amebiasis, the most effective is considered to be metronidazole. However, with regard to the treatment of asymptomatic carriers of amoebic dysentery (the primary vector for this disease), it is generally felt that its use incurs more treatment failures than result from the use of purely luminal amoebicides, and the latter are thus preferred. Therefore, the use of organophosphonate compounds in such manner, as for example, in combination with metronidazole in the treatment of the asymptomatic amoebic carrier state, is fully contemplated by the present invention.

Some organophosphonate compounds have been observed to cause nausea, increased frequency of bowel movements, loose bowel movements and diarrhea. Thus, in the treatment of amoebic dysentery, in which diarrhea is already a problem, appropriate measures should be taken to assure adequate hydration of the patient.

When an organophosphonate compound such as EHDP is used to control pyrophosphate utilizing microorganisms in industrial processes, for example, to control the propionibacteria of Swiss cheese as undesirable contaminants in the production of Gouda cheese, a concentration of phosphonate which will achieve control of the microorganism in the particular industrial process involved can readily be determined by standard microbiological techniques. See, for example, A. L. Barry, *The Antimicrobic Susceptibility Test: Principles and Practices* (1975), the disclosures of which are fully incorporated herein by reference. The organophosphonate EHDP has been found to produce inhibition of *E. histolytica in vitro* at a level of 500 micrograms per cc, although different levels may be necessary for inhibition of Propionibacteria, depending upon conditions.

The following non-limiting examples illustrate the industrial applicability of the present invention.

INDUSTRIAL APPLICABILITY

EXAMPLE I

An adult human patient suffering from amoebic dysentery is administered ethane-1-hydroxy-1,1-diphosphonate disodium in a dosage of 5 mg. per kg. per day. The causative organism *E. histolytica* is effectively controlled.

The ethane-1-hydroxy-1,1-diphosphonate of Example I is replaced with an equivalent amount of a methanehydroxy diphosphonate, dichloromethanediphosphonate, propane-3-amino-1,1-diphosphonate or nonane, 1,1-diphosphonate, and equivalent results are secured.

The ethane-1-hydroxy-1,1-diphosphonate of Example I is administered conjointly with 25 mg/kg/day of metronidazole in the treatment of the asymptomatic amoebic carrier state, and eradication of the carrier state in the afflicted individual is achieved.

EXAMPLE II

Methanediphosphonate disodium is added to milk used in making Gouda cheese at a two millimolar concentration. The phosphonate compound effectively deactivates the metabolic processes of Propionibacteria contaminants, and the propionibacteria are thus unable to impart undesirable off-flavor to the cheese.

EXAMPLE III

Carbonyldiphosphonic acid is incorporated into apple cider in a 5 millimolar concentration to retard spoilage. The carbonyldiphosphonate effectively controls species of Acetobacter, and thus prevents conversion of the cider to vinegar.

EXAMPLE IV

Drinking water in a geographical region with poor sanitation is treated with sodium dichloromethane diphosphonate tablets to provide a 10 millimolar concentration of the dichloromethane diphosphonate. *E. histolytica* present in the water are controlled, and the water can be consumed without risk of amoebic dysentery.

EXAMPLE V

A monkey with amoebic disease is administered nonane 1-hydroxy-1,1-diphosphonic acid in a dosage of 25 mg/kg/day. The metabolism of the causative organism *E. histolytica* is effectively disrupted and the symptoms of amoebic disease subside.

What is claimed is:

1. A method for treating amoebiasis comprising administering to a human or lower animal in need of such treatment from about 0.1 to about 5 milligrams/kilogram body weight/day of a geminal diphosphonate compound having the formula

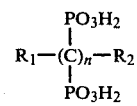

wherein n is an integer from 1 to about 10, $R_1$ is selected from the group consisting of hydrogen, alkyl containing from 1 to about 20 carbon atoms, alkenyl containing from 2 to about 20 carbon atoms, phenyl, napthyl, phenylethenyl, benzyl, halogen, amino, dimethylamino, diethylamino, N-hydroxy-N-ethylamino, acetylamino, $-CH_2COOH$, $-CH_2PO_3H_2$, $-CH(PO_3H_2)(OH)$ and $-CH_2CH(PO_3H_2)_2$, and $R^2$ is selected from the group consisting of hydrogen, methyl, ethyl, propyl, butyl, amino, benzyl, halogen, hydroxyl, $-CH_2COOH$, $-CH_2PO_3H_2$, and $-CH_2CH_2PO_3H_2$, or a pharmaceutically-acceptable salts and mixtures thereof.

2. A method according to claim 1 wherein the geminal diphosphonate compound is a member selected from the group consisting of ethane-1-hydroxy-1,1-diphosphonic acid, dichloromethane diphosphonic acid, methane hydroxy diphosphonic acid, nonane 1,1-diphosphonic acid, aminomethane diphosphonic acid, ethane-1-amino-1,1-diphosphonic acid, methane diphosphonic acid, nonane-1-hydroxy-1,1-diphosphonic acid, propane-3-amino-1,1-diphosphonic acid, the pharmaceutically acceptable salts of the above compounds, and mixtures thereof.

* * * * *